United States Patent [19]

Hirsch et al.

[11] Patent Number: 5,428,132
[45] Date of Patent: Jun. 27, 1995

[54] CONJUGATE AND METHOD FOR INTEGRATION OF FOREIGN DNA INTO CELLS

[75] Inventors: Raphael Hirsch, Rockville; Francois Hirsch, Bethesda, both of Md.

[73] Assignee: United States of America, Washington, D.C.

[21] Appl. No.: 1,903

[22] Filed: Jan. 7, 1993

Related U.S. Application Data

[63] Continuation of Ser. No. 815,905, Dec. 31, 1991, abandoned, which is a continuation of Ser. No. 643,091, Feb. 22, 1991, abandoned, which is a continuation of Ser. No. 255,837, Oct. 11, 1987, abandoned.

[51] Int. Cl.$^6$ .................... A61K 39/00; C12N 15/00
[52] U.S. Cl. .................... 530/387.1; 435/172.3; 530/391.1; 530/391.5; 935/52
[58] Field of Search ............ 435/6, 7, 172.3, 7.2, 435/7.21, 172.1; 436/63, 94; 530/387, 388, 389, 387.1, 391.1, 395.5; 935/52, 54, 55; 536/23.1–23.6

[56] References Cited

U.S. PATENT DOCUMENTS

| | | | |
|---|---|---|---|
| 4,592,998 | 6/1986 | Avrameas et al. | 435/6 |
| 4,692,416 | 9/1987 | Diamond | 436/508 |
| 4,748,111 | 5/1988 | Dattagupta et al. | 435/6 |

OTHER PUBLICATIONS

Revet et al, EMBO J. 3: 3353 (1984).
Dawkins, *The Extended Phenotype*, 1990, Oxford University Press, Oxford, pp. 85, 86, and 287.
Chien et al; Nature 309: 322 (1984).
American Type Culture Collection Catalogue of Cell Lines & Hybridomas, 5th Edition, 1985, p. 228.
Seeburg; DNA 1: 239 (1982).
Promega Biological Research Products, 1988/89 Catalog, section 10, p. 8.
Kubota et al; Chem. Abstr. 104: 32740y (1986).
Yoshikawa et al; Chem. Abstr. 104: 18372y (1986).

*Primary Examiner*—James Martinell
*Attorney, Agent, or Firm*—Knobbe Martens Olson & Bear

[57] ABSTRACT

The present invention describes a DNA-antibody conjugate and a method for integration of foreign DNA into cells in a tissue-specific manner by conjugating the foreign DNA with a target specific antibody.

14 Claims, No Drawings

CONJUGATE AND METHOD FOR INTEGRATION OF FOREIGN DNA INTO CELLS

This application is a continuation of application Ser. No. 07/815,905, filed Dec. 31, 1991, (now abandoned) which is a continuation of application Ser. No. 07/643,091, filed Jan. 22, 1991, (now abandoned), which is a continuation of application Ser. No. 07/255,837, filed Oct. 11, 1987, now abandoned.

TECHNICAL FIELD

The present invention is generally related to the techniques of integrating foreign DNA into cells. More particularly, the present invention is related to integrating foreign DNA into cells in a tissue or cell-specific manner by conjugating antibodies to DNA, this method being designated herein as "antifection."

BACKGROUND OF THE INVENTION

The methods presently available for integrating DNA into cells include transfection using calcium phosphate, DEAE Dextran, electroporation, infection with viruses, cell fusion, liposome DNA carriers and microinjection. However, these techniques often have low efficiency, cannot be performed in vivo and lack target specificity. In contrast, the method of the present invention allows target-specific DNA delivery and is applicable for in vivo transformation and gene therapy.

SUMMARY OF THE INVENTION

It is, therefore, an object of the present invention to provide an antifection method for tissue-specific, integration of foreign DNA by linking the foreign DNA to a target-specific antibody.

It is a further object of the present invention to provide an antifection method for treating genetic disorders by selectively integrating the DNA into specific tissues or cells which are the loci of gene defect.

It is an additional object of the present invention to provide an antifection method of tagging cells with Genetic markers.

It is a still further object of the present invention to induce tolerance to foreign transplantation antigens by antifecting susceptible target tissues with these antigens.

It is yet another object of the present invention to provide an antibody-DNA conjugate.

A further object of the present invention is to provide a unique method of integrating Genes into cells in vitro for various uses such as the expression of gene products or immortalization of cells.

Other objects and advantages of the present invention will become evident from the following detailed description of the invention.

DETAILED DESCRIPTION

These and other objects, features and many of the attendant advantages of the invention will be better understood upon a reading of the following detailed description.

The integration of foreign DNA into cells in a tissue-specific manner by employing direct conjugation of target-specific antibodies to the DNA is disclosed.

The method of the present invention comprises: (a) preparing a conjugate of foreign DNA to be integrated into target cells, with an antibody having binding affinity with a surface antigen of the cells into which said DNA needs to be integrated; then (b) binding of the conjugate of step (a) to the cells into which said DNA needs to be integrated; an expression of the protein product of said DNA by said cells being indicative of integration of said DNA into said cells.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. Unless mentioned otherwise, the techniques employed herein are standard methodologies well known to one of ordinary skill in the art.

The term "conjugation" as used herein means directly linking, coupling, binding and the like of the foreign DNA with target-specific antibodies, either chemically, electrostatically, non-covalently or by other techniques such as the production of hybrid antibodies which recognize both the DNA and a target antigen.

The term "stable" or "long term" as used herein means that the expression of the integrated gene continues in a non-transient manner, as these terms are commonly understood by one of ordinary skill in the art to which this invention belongs.

The invention is now illustrated by the following examples.

EXAMPLE 1

Two plasmids were used to antifect two different cell lines as follows:

Plasmid #1. a plasmid containing both the neomycin resistance gene and rat growth hormone gene.

Plasmid #2. a plasmid containing only the neomycin resistance gene.

Various steps are now outlined.

(a) 500 ug of naked plasmid was dissolved into 0.1M potassium phosphate, pH 8 to which was added benzoquinone 50 mM in ethanol and 1/10 volume 1M potassium phosphate. The solution was kept at room temperature (22°–25° C.) in the dark for about one hour.

(b) The solution was passed through a G25 column (Pharmacia) which had been prewashed with Baker's yeast RNA (5 ml of a 10 mg/ml solution) to prevent binding of DNA to the column. The column was equilibrated with 0.15M NaCl, and the plasmid solution from step (a) was added. The first fraction, containing the activated DNA, was collected.

(c) Hamster monoclonal antibody 145-2C11(Leo et al, 1987, Proc. Nat'l. Acad. Sci., USA, 84:1374) directed against the murine CD3 antigen, at a concentration of 10 mg/ml in borate buffered saline, pH 8.5, was then added as follows:

2/5 of the collected fraction from step (b) was mixed with 200 ul of antibody (2 mg) to give a ratio of DNA:antibody of about 1:10.

2/5 of the collected fraction from step (b) was mixed with 20 ul of antibody (0.2 mg) to give a ratio of DNA:antibody of 1:1.

1/10 volume of carbonate-bicarbonate buffer, pH 8.5 was then added to each sample, which was incubated for about 24 hours at 4°.

(d) The reaction was stopped by adding 1/10 volume lysine, pH 7, at room temperature for about 2 hours.

(e) In order to separate free antibody from conjugates, the samples were put into dialysis tubing which was laid lengthwise in a horizontal electrophoresis system containing Tris-EDTA buffer, pH 7. The samples were subjected to a current of 40 mVolts overnight (12-16 hrs). The dialysis tubing was tied at the middle, separating the DNA-containing fraction, which had migrated towards the positive electrode, from free antibody, which had migrated towards the negative electrode.

(f) The contents of each sample were treated by addition of gentamicin and penicillin-streptomycin at room temperature for about 24 hours.

(g) The presence of conjugates was confirmed by standard ELISA assay in which anti-DNA antibody was bound to plastic wells, followed by incubation with the conjugates which was then followed by incubation with peroxidase-labeled goat anti-hamster Ig.

(h) Continued activity of the monoclonal antibody after conjugation was confirmed by the ability of the conjugates to block staining of the CD3+ cell line 2B4 by FITC-coupled 145-2C11, as measured by standard flow cytometry.

(i) Conjugates were then incubated with 3 cell lines:
2B4:a CD3+ murine T cell hybridoma
EL4:a CD3+ murine T cell tumor line
21:22:a CD3− mutant: of 2B4 to which 145-2C11 does not bind.

$0.1 \times 10^5$ cells were placed in 2 ml of media (RPMI with 10% fetal calf serum and nutrients). 30–50 ul of conjugate solution was added to each well. After 48 hours, the antibiotic G418 was added at a concentration previously found to kill the above cell lines (400 ug/ml for 2B4 and 21.22, 100 ug/ml for EL4). All wells containing cells-without conjugates had 100% mortality of cells. Resistant cells grew out in wells containing conjugates as follows: Experiment #1:

| plasmid | DNA:antibody (by weight) | wells containing resistant cells | |
|---|---|---|---|
| #1 | 1:10 | 2B4 --1 of 2 | |
|  | 1:1 | 2B4 --0 of 2 | |
|  | 1:10 | 21.21 --0 of 2 | |
|  | 1:1 | 21.22 --0 of 2 | |
| — | — | 2B4 --0 of 4 | Control |
| — | — | 2B4 --0 of 4 | |

(21.22 is CD3 and, therefore, would not be expected to be antifected)

| Experiment #2: | | | |
|---|---|---|---|
| #2 | 1:10 | 2B4 --1 of 2 | |
|  |  | EL4 --1 of 2 | |
|  | 1:1 | 2B4 --1 of 2 | |
|  |  | EL4 --1 of 2 | |
| — | — | 2B4 --0 of 4 | Control |
| — | — | EL4 --0 of 4 | Control |

Resistant 2B4 cells were transferred to media containing 800 ug/ml of G418 and EL4 cells were transferred to media containing 200 ug/ml G418 and the cells allowed to grow in these media for about 4 weeks.

DNA from resistant cells was analyzed by Southern blot analysis by probing with the neomycin resistance gene. The results indicated that cell lines A, B, C, D, and E all contained the neomycin resistance gene, while control cells did not, indicating that the gene had been incorporated into the cells' DNA and that stable long term expression had been achieved.

EXAMPLE 2

Another means of conjugating antibody to DNA is now described. An antibody directed against DNA (anti-DNA antibody) is hetero-conjugated to an antibody directed against the cell using the method described by Segal (J. Expt. Med., 1984, 160:1686). This heteroconjugate is then allowed to interact with the DNA resulting in the formation of a DNA-heteroconjugate linkage which will recognize the target antigen. Alternatively, a universal reagent is produced by heteroconjugating an anti-DNA antibody to an anti-Ig antibody. This heteroconjugate is then used to conjugate any DNA to any antibody of the isotype recognized by the anti-Ig antibody following standard methodology.

EXAMPLE 3

In vivo antifection:

DNA-antibody conjugate prepared in accordance with the present invention is used to incorporate genes into cells in vivo as follows: After conjugating the desired gene to the desired antibody as described, the conjugate is administered to the patient or animal, either once or a number of times. The amount to be administered and the frequency of administration depend upon such factors as the stage of development, mass of the tissue, body weight and the like and can be easily adjusted by one of ordinary skill in the art. Following introduction of the conjugate, the conjugated antibody circulates until it encounters a cell with the appropriate antigen on its surface. The conjugate binds to this cell via the antibody portion, modulation or endocytosis of the conjugate occurs and the DNA portion thereof then gets integrated into the cell genome.

Of course, targeting of DNA to specific cell types depends on the selection of the antibody. Without being bound to any specific theory, it is postulated that targeting occurs by binding of the antibody (to which DNA is conjugated) to the cell surface antigen against which the antibody is directed, followed by modulation or endocytosis of the antigen intracellularty along with the antibody-DNA conjugate, thereby achieving gene delivery to the specific cell type, such as demonstrated herein of the antifection of the T lymphocytes using an antibody against T cells (vide supra). Similarly, the process of the present invention could be used to infect liver cells by using anti-hepatocyte antibodies, bone marrow stem cells with anti-stem cell antibodies, etc.

Of course, the strategy of the present invention could also be used in vitro as a means of integrating DNA into cells for which known methods are ineffective and for transforming cells. For example, T cells could be immortalized by antifection with an oncogene in order to supply a ready source of lymphokines such as interleukin 2, tumor necrosis factor and the like. Alternatively, a gene coding for a hormone, drug or other product could be antifected into an immortalized cell in order to produce the desired product in large quantities. Furthermore, the cells could be removed from the body, antifected in vitro with a gene coding for a specific product, and then returned to the patient. Such manipulations are particularly useful for treating genetic disorders especially when used in vivo to selectively integrate DNA into specific tissues to alleviate inherited diseases caused by a specific gene defect. For example, antifection of genes into liver cells could alleviate inborn errors of metabolism or hemophilia, antifection of genes into hematopoietic cells could alleviate sickle-cell anemia, thalassemia, adenosine-deaminase deficiency and the like. Moreover, antifection could allow integration of larger DNA fragments than is possible with other methods, thus allowing the use of genomic DNA and the gene's natural promoter to obtain increased yield of antifected cells and physiologic gene expression.

Thus, the technique illustrated herein has numerous applications which are easily achievable by one of ordinary skill in the art.

Recently, Goud, et al, 1988 (Virology 163: 251-254) attempted to integrate a neomycin-resistance gene, which had been recombined into a murine Moloney retrovirus, into human HEp2 cells by the use of antibodies. An antibody against gp70 envelope vital protein was linked to an antibody against the human transferrin receptor by a sheep anti-murine k light chain antibody. It should be noted that while internalization of viral particles occurred, no expression of the neomycin-resistance gene was obtained. The expression of the neomycin-resistance by the process of the present invention is indeed a noteworthy contrast.

Wang, et al, (1987) (PNAS 84, 7851-7855) employed "pH-sensitive immunoliposomes" and observed expression of the CAT gene after 24 hours in some of the RDM-4 cells. However, long-term expression was not seen. It should be noted that the present invention is quite different from the Wang et al, supra, in that the present invention conjugates the naked DNA directly to the antibody instead of employing liposomes containing DNA and antibody. Moreover, immuno-liposomes are not specific for the target antigen because they can fuse to any cell.

In summary, the unique method of the present invention for the first time provides target-specific in vivo and in vitro stable integration of DNA into cells, which was heretofore not possible.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A DNA-antibody conjugate, comprising a DNA sequence capable of expressing a functional protein product, in eukaryotic cells, said DNA sequence conjugated to an antibody having binding affinity for a cell surface antigen, so that when said conjugate is antifected into cells expressing said surface antigen, integration of said DNA sequence into the genomic DNA of said cells results.

2. The conjugate of claim 1, wherein said DNA encodes a selectable marker.

3. The conjugate of claim 2, wherein said selectable marker confers neomycin resistance to eukaryotic cells.

4. The conjugate of claim 1, wherein said antibody binds specifically to a cell surface protein.

5. The conjugate of claim 4, wherein said cell surface protein is CD3.

6. The conjugate of claim 1, wherein said antibody is a monoclonal antibody.

7. The conjugate of claim 1, wherein said DNA is linked to said antibody by a covalent bond.

8. The conjugate of claim 1, wherein said antibody is a heteroconjugate that comprises a first antibody having binding affinity for a cell surface antigen and a second antibody.

9. The conjugate of claim 8, wherein said second antibody binds specifically to DNA.

10. A DNA-antibody conjugate that binds specifically to a cell surface antigen, said conjugate being produced by a process comprising:
obtaining a DNA sequence capable of expressing a functional protein product, in eukaryotic cells;
obtaining an antibody that binds specifically to said cell surface antigen; and
linking said antibody to said DNA sequence.

11. The conjugate of claim 10, wherein said antibody binds specifically to CD3.

12. The conjugate of claim 10, wherein said DNA encodes a protein conferring resistance to neomycin.

13. A DNA-antibody conjugate, comprising a DNA sequence and an antibody, wherein said DNA encodes a polypeptide, wherein said antibody is specific for a eukaryotic cell surface antigen, and wherein antifection of said conjugate into eukaryotic cells expressing said surface antigen results in expression of said polypeptide.

14. The conjugate of claim 13, wherein antifection of said conjugate results in integration of said DNA sequence into the genomic DNA of said cells.

* * * * *